(12) United States Patent
Wang

(10) Patent No.: US 7,125,385 B1
(45) Date of Patent: Oct. 24, 2006

(54) INSTRUMENT FOR DETERMINING INTRATESTICULAR DOSE AND METHOD FOR DETERMINING A DOSE

(75) Inventor: Min Wang, Columbia, MO (US)

(73) Assignee: Technology Transfer, Inc., Columbia, MO (US)

( * ) Notice: Subject to any disclaimer, the term of this patent is extended or adjusted under 35 U.S.C. 154(b) by 472 days.

(21) Appl. No.: 10/413,424

(22) Filed: Apr. 14, 2003

(51) Int. Cl.
 *A61B 5/103* (2006.01)
 *A61B 5/117* (2006.01)

(52) U.S. Cl. .......................... 600/587; 33/512; 33/571

(58) Field of Classification Search ................ 600/587; 33/511, 512, 513, 679.1, 545, 571
See application file for complete search history.

(56) References Cited

U.S. PATENT DOCUMENTS

| | | | |
|---|---|---|---|
| 1,981,911 A | | 11/1934 | Engelsman .................. 33/512 |
| 2,874,478 A | * | 2/1959 | Faulconer .................... 33/810 |
| 3,478,435 A | | 11/1969 | Cook .......................... 33/511 |
| 4,097,997 A | * | 7/1978 | Bjornson ................... 33/1 SD |
| 4,156,427 A | * | 5/1979 | Fahim ......................... 604/506 |
| 4,233,743 A | | 11/1980 | Flick ............................ 33/512 |
| 4,599,800 A | | 7/1986 | Wyrwich et al. ............. 33/802 |
| 4,713,888 A | * | 12/1987 | Broselow ....................... 33/512 |
| 5,027,520 A | | 7/1991 | Finnegan ...................... 33/195 |
| 5,070,080 A | * | 12/1991 | Fahim ........................ 514/53 |
| 5,156,161 A | | 10/1992 | Lollar ......................... 600/587 |
| 5,164,181 A | * | 11/1992 | Silver et al. ............. 424/94.63 |
| 5,183,055 A | | 2/1993 | Seager ........................ 600/587 |
| 5,193,287 A | * | 3/1993 | Coulter et al. ............. 33/555.4 |
| 5,249,366 A | | 10/1993 | Takahashi et al. ............ 33/811 |
| 5,483,751 A | * | 1/1996 | Kodato ........................ 33/811 |
| 6,110,200 A | | 8/2000 | Hinnenkamp .............. 623/2.11 |
| 6,430,830 B1 | | 8/2002 | Segal .......................... 33/513 |
| 6,761,890 B1 | * | 7/2004 | Meloen et al. ........... 424/185.1 |

* cited by examiner

*Primary Examiner*—Max F. Hindenburg
*Assistant Examiner*—Rene Towa
(74) *Attorney, Agent, or Firm*—Grace J. Fishel

(57) ABSTRACT

An instrument for measuring the size of a testis has a pair of relatively displaceable jaws with testis contacting surfaces. The spacing between the jaws is displayed on a scale calibrated to a recommenced dose of a chemical sterilant at a given concentration for the testis measured for sterilizing a male animal having scrotal testes. The instrument is used to determine the appropriate dose to be administered the animal, each testis of which should be independently measured as the size of the testicles may different in the same animal.

4 Claims, 3 Drawing Sheets ness of the invention will be in part apparent and in part pointed
INSTRUMENT FOR DETERMINING INTRATESTICULAR DOSE AND METHOD FOR DETERMINING A DOSE

BACKGROUND OF THE INVENTION

1. Field of the Invention

The present invention relates to an instrument for determining an appropriate dose of a liquid chemical sterilant to be injected into a testis of an animal having scrotal testes and to a method for determining the dose with the instrument.

2. Brief Description of the Prior Art

Various chemical agents have been injected into the testes for the purpose of interfering with the production of sperm in the seminiferous tubules. Many effective chemicals have been found too harsh to be used practically. An effective and biologically acceptable chemical sterilant was described in U.S. Pat. Nos. 4,937,234 and 5,070,080 to Fahim. In the '080 patent, the chemical sterilant was injected into the midline at the side or bottom of each testis. Depending upon the dose administered, spermatogenesis in the seminiferous tubules was completely stopped. It was later found that if the injection is given into the dorsal cranial portion of the testis, lesser amounts of chemical sterilant is needed to effect complete sterilization.

The effective dose depends on the concentration of the active ingredients in the aqueous solution and the size of the testis. Injecting too large a volume may rupture the testis and too large a dose may be harmful to the animal. Testis size, however, does not correlate with body weight so that the dose cannot be determined by weighing the animal. For example, dogs of different breeds having the same weight may have different sized testes. Even dogs of the same breed and having the same weight may have different sized testes. It also occurs that the testes of the same dog may be different in size. Hence the size of the testis of each animal must be measured to determine the dose to be injected to effect sterilization.

BRIEF SUMMARY OF THE INVENTION

In view of the above, it is an object of the present invention to provide an instrument for determining the appropriate volume of a chemical sterilant at a given concentration to be injected into a testis of an animal to effect sterilization. It is another object to provide a method for determining the appropriate dose. Other objects and features of the invention will be in part apparent and in part pointed out hereinafter.

In accordance with the invention, an instrument for measuring the size of a testis has a pair of relatively displaceable jaws with testis contacting surfaces. The spacing between the jaws is displayed on a scale calibrated to a recommended dose of a chemical sterilant at a given concentration for the testis measured. The instrument can be used to determine the appropriate dose to be administered to a mammalian animal with scrotal testes, each testis of which should be independently measured as the size of the testicles may different in the same animal.

The invention summarized above comprises the construction and method hereinafter described, the scope of the invention being indicated by the subjoined claims.

BRIEF DESCRIPTION OF THE SEVERAL VIEWS OF THE DRAWING

In the accompanying drawings, in which one of various possible embodiments of the invention is illustrated, corresponding reference characters refer to corresponding parts throughout the several views of the drawings in which.

DETAILED DESCRIPTION OF THE INVENTION

The dose delivered of a chemical sterilant as described in U.S. Pat. Nos. 4,937,234 and 5,070,080 is a function of the concentration of the active ingredients and the volume of chemical sterilant injected. The chemical sterilant can be used with domesticated and feral mammals having scrotal testes. This includes pets and livestock such as dogs, cats, horses, cattle, pigs and sheep and wild animals such as bears, wolves, deer and so forth. The effective dose required depends upon the species of animal (e.g., cats require a larger dose than dogs) and the size of the animal's testes.

The chemical sterilant described in the '080 patent is biologically acceptable, effective and non-injurious to the animal. The chemical sterilant is a mineral gluconate salt and an amino acid capable of forming an aqueous solution neutralized to a pH in the range of 6.0 to 7.5. Physiologically acceptable minerals include zinc, calcium, iron, magnesium, manganese and the like and illustrative mineral salts include zinc gluconate.

Zinc gluconate can be neutralized to form a stable aqueous solution with the following amino acids: alanine, valine, isoleucine, proline, glycine, serine, threonine, asparagine, glutamine, lysine, arginine, histidine and mixtures thereof. The solution cannot be formed with cysteine, tyrosine, aspartic acid or glutamic acid and among the basic amino acids, arginine is preferred when the mineral gluconate salt is zinc gluconate.

In neutralizing mineral salts such as zinc gluconate, it is preferred that the mineral salts and the amino acid be present in substantially equimolar amounts. Suitable formulations for use as a chemical sterilant are formed with a molar amount of mineral salt such as zinc gluconate to amino acid such as arginine from about 0.05M:2.0M to about 2.0M:0.05M, preferably from about 0.05M:0.3M to about 0.3M:0.05M and most preferably from about 0.1M:0.2M to about 0.2M:0.1M and neutralized to a pH in the range from about 6.0 to about 8.0, preferably from about 6.5 to about 7.5 and most preferably 7.0. The solution is formed and then sterile filtered into sterile serum vials.

Figure 1:
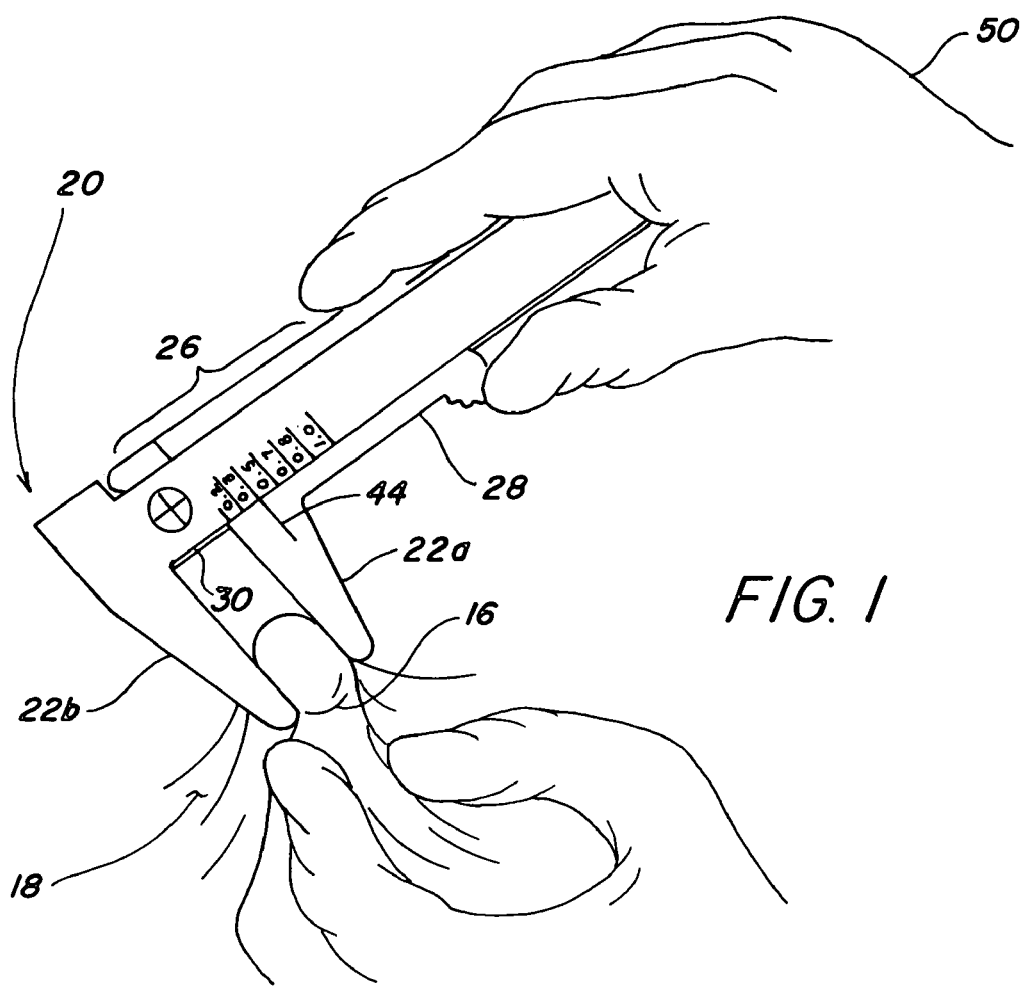
FIG. 1 is a perspective view of an instrument for determining an appropriate dose of a liquid chemical sterilant to be injected into a testis in accordance with the present invention.
Figure 2:
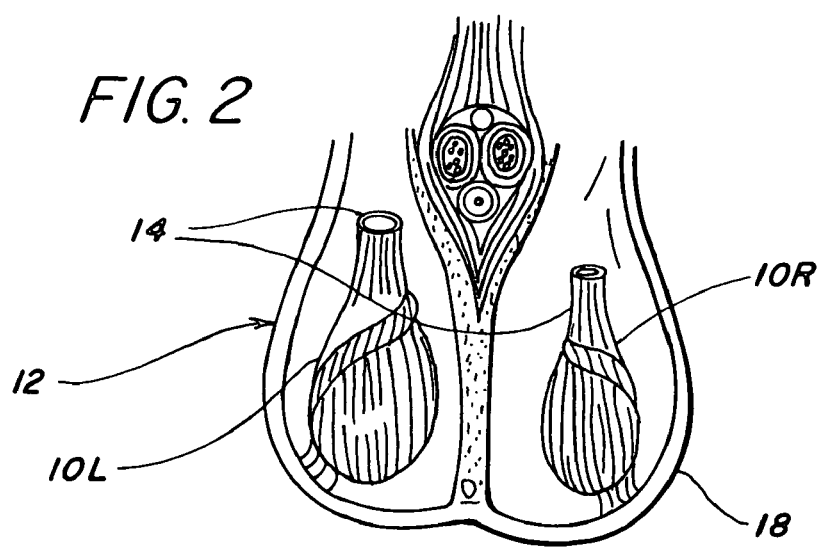
FIG. 2 is a transverse section of a scrotal testes.
Figure 3:
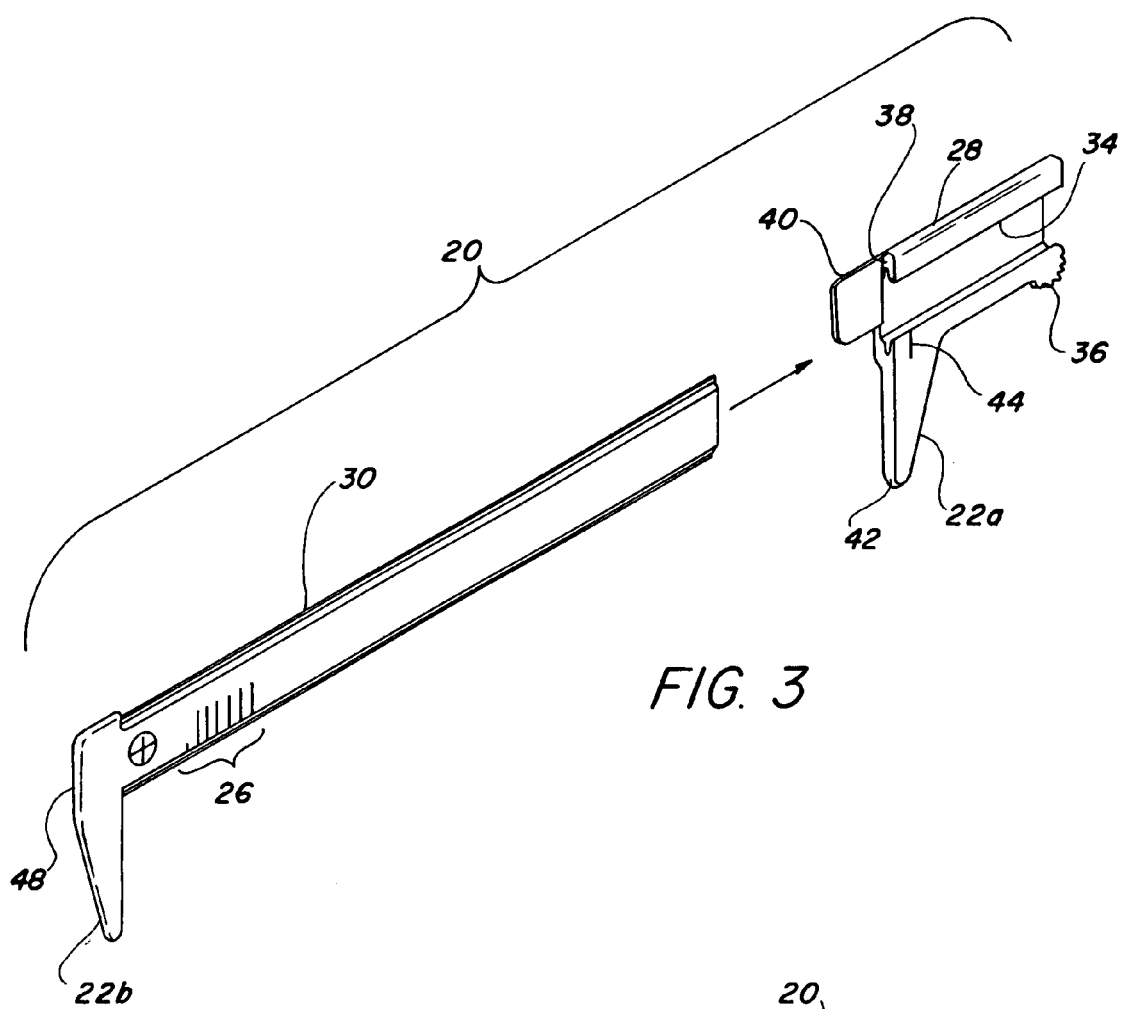
FIG. 3 is an exploded perspective view of the instrument of FIG. 1.

Mammalian scrotal testes 10 as shown in FIG. 2 are oval in form and are suspended in a scrotum 12 by spermatic cords 14. They are longer than they are wide and are compressed laterally. Testicular measurement can be made by extending the testicle into scrotum 12 until a firm testicular outline 16 is seen through the scrotum wall 18 as shown in FIG. 1. Testis 10 can then be measured, advantageously in the anteroposterior direction at its widest part as described below. A lengthwise measurement can also be made but the testicle is more compressible in that dimension which complicates making an accurate measurement.

A reference set of data is taken. The testes of a population of animals of a particular species, for examples dogs or cats, are measured and the amount of chemical sterilant necessary to effect sterilization determined clinically. A table is developed with testicle size correlated with volume of chemical sterilant at a given concentration necessary to effect sterilization. For example, when the chemical sterilant consists of an aqueous solution containing 13.1 mg/ml of zinc as zinc gluconate neutralized by 34.8 mg/ml of l-arginine with the pH adjusted to 7.0 with hydrochloric acid, the recommended dose per testicle in a dog three months to ten months of age based on testicle width measured at its widest part was clinically determined to be as follows:

Dose Corresponding to Testicular Width

| Range of Testicular Width (mm) | Dose Administered (ml) |
| --- | --- |
| 10–12 | 0.2 |
| 13–15 | 0.3 |
| 16–18 | 0.5 |
| 19–21 | 0.7 |
| 22–24 | 0.8 |
| 25–27 | 1.0 |

Once a reference set of data has been taken and the recommended dose per testicle based on size determined, an operator can determine the effective dose to be given to an animal which is to be sterilized with an instrument 20 in accordance with the present invention.

Figure 4:
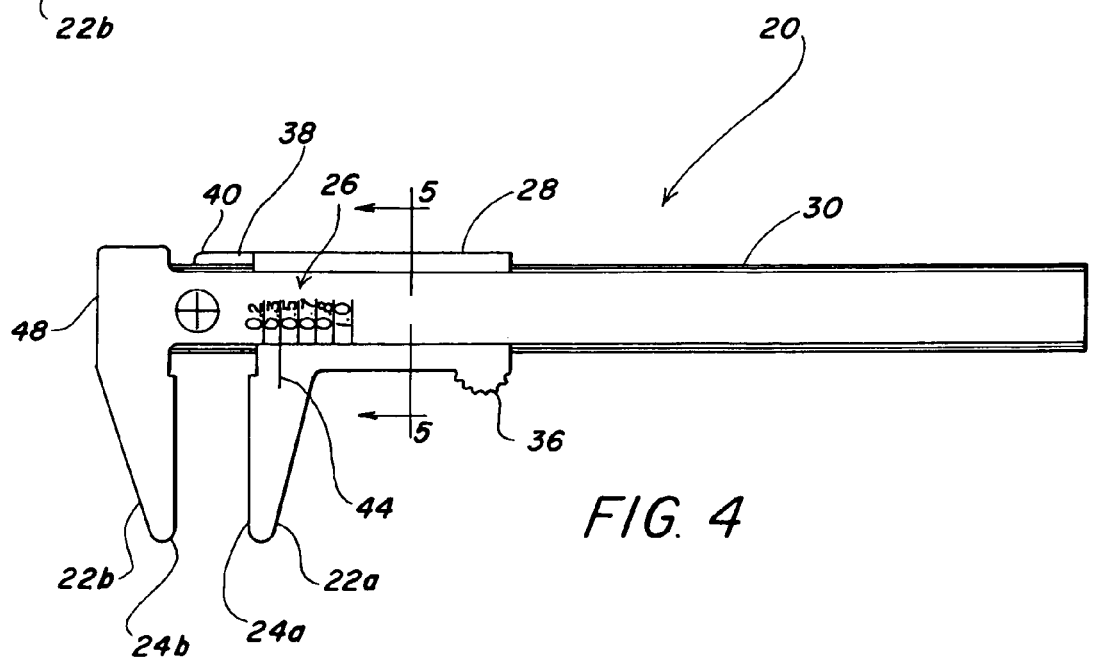
FIG. 4 is a front side elevational view of the instrument.

Referring to FIGS. 1, 3–4 and 6, instrument 20 has a pair of relatively displaceable jaws 22 with testis 10 contacting surfaces 24 whose spacing is displayed on a scale 26 calibrated to a recommended dose of a chemical sterilant at a given concentration for the testis measured. Scale 26 as shown in FIGS. 1 and 4 is calibrated with the data shown in the above table for puppies between three and ten months of age. It will be understood that scale 26 will be different for other animals and for sexually mature dogs. Cats, for example, require a higher dose than dogs based on comparable testicle size. Cats, also, should be sexually mature before sterilization is undertaken.

While the particular instrument 20 shown in the drawings is a sliding caliper, it will be appreciated that instrument 20 may be a screw-type micrometer, bow micrometer, pivotal caliper device or the like. Instrument 20 may be a constant pressure gauge although this is not necessary when the testis is measured in the anteroposterior direction because the testis is not very compressible laterally. On the other hand, when the measurement is taken along the long axis of the testis, a constant pressure gauge may be preferred.

Figure 5:
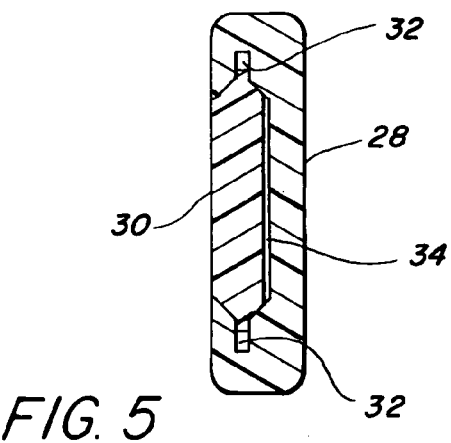
FIG. 5 is a sectional view taken along the plane of 5—5 in FIG. 4; and, FIG. 6 is a rear side elevational view of the instrument.
Figure 6:
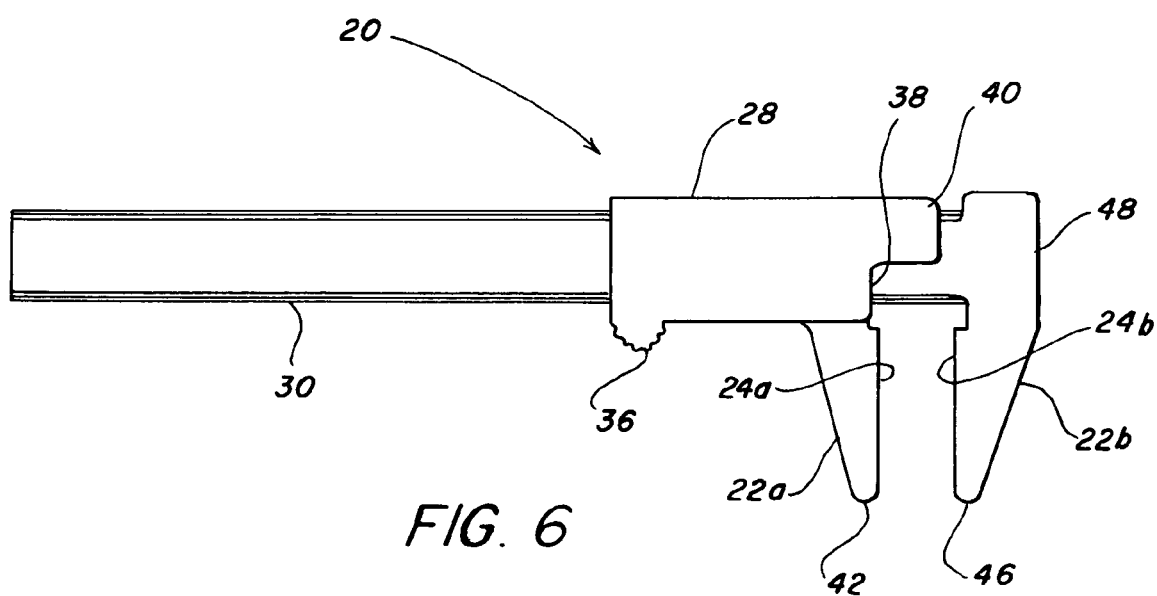

As shown in the drawings, instrument 20 is a sliding caliper molded in two parts including a sleeve 28 and a rule 30. Rule 30 is keyed 32 in a slot 34 in sleeve 28 as shown in FIG. 5. A jaw 22a projects at one side from a top end region of sleeve 28 and an convex thumb grip 36 projects, on the same side as jaw 22a from the bottom end region of sleeve 28.

Slot 34 has a straight longitudinal axis and jaw 22a extends at a right angle to the axis of slot 34 with a flat top edge making up testis 10 contacting surface 24a. Contacting surface 24a is slightly elevated above a top end edge 38 of sleeve 28. An ear 40 extends from the bed of slot 34 above contacting surface 24a and top end edge 38. Jaw 22a tapers away from sleeve 28 to a small-dimensioned rounded tip 42. On at least one side of slot 34, an indicator line or pointer 44 is formed in sleeve 28.

Rule 30 is an elongate generally flat member having a jaw 22b projecting at right angles at a top end. Jaw 22b has a flat bottom edge making up testis 10 contacting surface 24b. Jaw 22b tapers away from contacting surface 24b to a small-dimensioned around tip 46. Scale 26 on rule 30 is expressed in volumetric units such as ml and is visible through slot 34. When contacting surfaces 24a and 24b touch, ear 40 underlies jaw 22b and reaches to a top end edge 48 of rule 30. It will be understood that the placement of indicator line 44 on sleeve 28 and scale 26 on rule 30 may be reversed such that indictor line 44 is on rule 30 and scale 26 is on sleeve 28.

In use as shown in FIG. 1, a puppy is placed in supine position, prior to which time the dog may be given a chemical restraint to prevent the dog from moving during the procedure. Scrotum wall 18 is prepared with an appropriate disinfectant. The use of alcohol with dogs is discouraged as it irritates the scrotum skin of some dogs.

An operator 50 then holds left testis 10L in one hand and extends the testis into scrotum wall 18 until testicular outline 16 is seen through the scrotum wall. Testis 10L is measured. As shown in FIG. 1, the measurement is taken with instrument 20 in the anteroposterior direction. Sleeve 28 is slid on rule 30 such that testis 10L is received at its widest part between jaws 22a and 22b. Sleeve 28 is then moved such that the spacing between the jaws is reduced and testis 10L is firmly gripped. The volume of chemical sterilant to be injected into testis 10L is then read off calibrated scale 26 by noting the position of indicator line 44 which is adjacent to scale 26. If indicator line 44 is below the lowest volume indicated, testis 10L is too small for injection with chemical sterilant. In like manner, if indicator line 44 is above the largest volume indicated, testis 10L is too large for injection. If indicator line 44 is between two volumes, testis 10L should be injected with the larger volume.

A record is made of the volume to be injected into the left testis 10L and the right testis 10R measured and a record made. It is necessary to measure both testes as they may differ in size as illustrated in FIG. 2. If the testes are of a suitable size for treatment, a syringe for the left testis 10L and a syringe for the right testis 10R is filled with chemical sterilant in the amount determined by the above procedure and testes injected in the dorsal cranial portion. It is recommended as a standard procedure to inject the left testicle first and then the right testicle to avoid confusion and re-injecting the same testicle. Injection should be done slowly because rapid injection may stimulate contraction of the seminiferous tubules and cause the chemical sterilant to leak from the injection site. The operator should not use excessive injection pressure to force the drug into the testicle. If resistance is felt, the injection should be discontinued.

In view of the above, it will be seen that the several objects of the invention are achieved and other advantageous results attained. As various changes could be made in the above construction and method without departing from the scope of the invention, it is intended that all matter contained in the above description or shown in the accompanying drawings shall be interpreted as illustrative and not in a limiting sense.

What is claimed is:

1. A method for determining a recommended dose of a chemical sterilant to be infected into a first and second scrotal testis of a mammal comprising:

a) providing an instrument for measuring a mammalian scrotal testis having a pair of relatively displaceable jaws with testis contacting surfaces whose spacing is displayed on a scale calibrated to a recommended dose of the chemical sterilant at a given concentration for the testis measured wherein the chemical sterilant is an aqueous solution comprising 13.1 mg/ml of zinc as zinc gluconate neutralized by 34.8 mg/ml of l-arginine with a pH adjusted in a range of 6.0 to 7.5 with hydrochloric acid;
b) placing a male animal to be sterilized in supine position;
c) holding the first testis of the animal and extending it until a testicular outline is seen through a scrotal wall;
d) placing the first testis between the jaws of the instrument and reducing a spacing between the jaws until the testis is firmly gripped;
e) reading the recommended dose on the scale;
f) repeating steps (c) through (e) for the second testis.

2. The method of claim 1 wherein the scale is calibrated for dogs.

3. The method of claim 1 wherein the scale is calibrated for cats.

4. The method of claim 1 wherein the scale is calibrated for puppies between three and ten months of age.

* * * * *